United States Patent [19]
Horrobin et al.

[11] Patent Number: 5,990,164
[45] Date of Patent: Nov. 23, 1999

[54] N-ALKYLPOLYHYDROXYAMINE SALTS OF POLYUNSATURATED FATTY ACIDS

[75] Inventors: David F. Horrobin, Stirling; Philip Knowles; Mehar Manku, both of Carlisle; John C. Stewart, Guildford, all of United Kingdom

[73] Assignee: Scotia Holdings PLC, United Kingdom

[21] Appl. No.: 08/930,701

[22] PCT Filed: Apr. 19, 1996

[86] PCT No.: PCT/GB96/00952

§ 371 Date: Mar. 17, 1998

§ 102(e) Date: Mar. 17, 1998

[87] PCT Pub. No.: WO96/33155

PCT Pub. Date: Oct. 24, 1996

[30] Foreign Application Priority Data

Apr. 20, 1995 [GB] United Kingdom .................. 9508023

[51] Int. Cl.$^6$ ................................................. A61K 31/215
[52] U.S. Cl. .......................... 514/560; 514/557; 514/558; 554/66; 554/68
[58] Field of Search ........................ 882/66, 68; 514/587, 514/588, 860

[56] References Cited

U.S. PATENT DOCUMENTS 1,985,424  12/1934  Piggott et al. ............................. 554/66
2,703,798  3/1955  Schwartz .................................... 554/66

FOREIGN PATENT DOCUMENTS 431130   3/1934  United Kingdom .
92 06984  4/1992  WIPO .
92/06984  4/1992  WIPO .

*Primary Examiner*—Deborah D Carr
*Attorney, Agent, or Firm*—Nixon & Vanderhye

[57] ABSTRACT

An N-alkylpolyhydroxyamine salt of an n-6 or n-3 essential fatty acid (EFA) that is beyond the 6-desaturation step, or of any polyunsaturated fatty acid, other than those belonging to the n-6 and n-3 series, having 16 to 26 carbon atoms and up to six double bonds, the double bonds being in the cis or trans configuration, the salt being formed with the fatty acid either as such or in the form of a covalent derivative, through the carboxyl group, of a bifunctional compound itself having a free acid function.

12 Claims, No Drawings

N-ALKYLPOLYHYDROXYAMINE SALTS OF POLYUNSATURATED FATTY ACIDS

This application is a 371 of PCT/GB96/00952 filed Apr. 19, 1996.

FIELD OF THE INVENTION

The invention relates to fatty acid derivatives.

BACKGROUND

Numerous previous patent applications by the inventors have documented important therapeutic actions of the n-6 and n-3 essential fatty acids. These essential fatty acids (EFAs) and their bodily conversion pathways are set out in Table 1 below.

TABLE 1

| n-6 EFA's | | n-3 EFA's |
| --- | --- | --- |
| 18:2n-6 | | 18:3n-3 |
| Linoleic acid, LA) | | (α-Linolenic acid, ALA) |
| ↓ | δ-6-desaturation | ↓ |
| 18:3n-6 | | 18:4n-3 |
| (γ-Linolenic acid, GLA) | | (Stearidonic acid) |
| ↓ | elongation | ↓ |
| 20:3n-6 | | 20:4n-3 |
| (Dihomo-γ-linolenic acid, DGLA) | | |
| ↓ | δ-5-desaturation | ↓ |
| 20:4n-6 | | 20:5n-6 |
| (Arachidonic acid, AA) | | (Eicosapentaenoic acid, EPA) |
| ↓ | elongation | ↓ |
| 22:4n-6 | | 22:5n-3 |
| (Adrenic acid) | | |
| ↓ | δ-4-desaturation | ↓ |
| 22:5n-6 | | 22:6n-3 |
| | | (Docosahexaenoic acid, DHA) |

The acids, which in nature are of the all-cis configuration, are systematically named as derivatives of the corresponding octadecanoic, eicosanoic or docosanoic acids, e.g. z,z octadeca-9,12-dienoic acid or z,z,z,z,z,z docosa-4,7,10,13,16,19-hexaenoic acid, but numerical designations based on the number of carbon atoms, the number of centres of unsaturation and the number of carbon atoms from the end of the chain to where the unsaturation begins, such as, correspondingly, 18:2n-6 or 22:6n-3, are convenient. Initials, e.g. EPA and shortened forms of the name e.g. eicosapentaenoic acid are used as trivial names in some of the cases.

The preferred fatty acids of the present invention are the ten n-6 and n-3 essential fatty acids that are beyond the 6-desaturation step, desirably in all -cis form, but the invention is not limited to them nor to acids in which the chain contains repeating —CH=CH—CH$_2$— units. Columbinic acid and α-parinaric acids, for example, are also suitable, being e,z,z-octadeca-5,9,12-trienoic acid and z,e,e,z-octadeca-9,11,13,15-tetraenoic acid, respectively.

The therapeutic actions include desirable effects in many different diseases including cardiovascular diseases, diabetes, skin diseases, inflammatory diseases and immunological diseases, cancer, psychiatric disorders, renal diseases, prostatic disorders and gastrointestinal and other diseases.

By their nature, EFAs are highly hydrophobic compounds which are soluble in water to a negligible extent. However, there are many reasons why it would be desirable to have a water soluble form of these compounds. Such water soluble derivatives may, for example be more easily absorbed from the gut via the hepatic portal system; may be given intravenously with ease; and may be used in many other ways such as in topical formulations, formulations for local administration, innovative oral formulations including drinks, enteral foods, and skin care preparations including lotions, shampoos, creams and so on.

Meglumine (N-methyl glucamine, an N-alkyl polyhydroxy amine) is an agent which is widely used in pharmaceutical formulations and which has an excellent safety profile. The formula is:

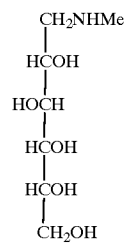

[C$_7$H$_{17}$NO$_5$; M.W. 195.2]

We have found that the meglumine derivatives of EFAs are highly water soluble and can therefore be used in many different ways in the formulation of pharmaceuticals, foods, nutritional supplements, skin care products and drinks of many different sorts. The invention can also be applied to a wide variety of other polyunsaturated fatty acids, other than those belonging to the n-6 and n-3 series, which have 16 to 26 carbon atoms, up to 6 double bonds, and with the double bonds in either the cis or trans configuration.

THE INVENTION

The invention provides water soluble N-alkylpolyhydroxyamine salts of polyunsaturated fatty acids as above, particularly the n-6 and n-3 essential fatty acids that are beyond the 6-desaturation step. These salts are stoichiometric and of the form (1) where A$^+$ is, in particular, protonated N-methyl glucamine (Meglumine), but also protonated glucamine or any other N-alkylpolyhydroxy amine, and FA⁻ is the anion of the EFA or other fatty acid:—

$$A^+FA^- \qquad (1)$$

The invention further relates to the formation of salts wherein the EFAs or other fatty acids are in the form of derivatives formed by covalent combination of the fatty acid, through the carboxy group and thus normally as an ester or amide, with a bifunctional compound having also a free acidic function. Examples are ascorbic acid, where the fatty acid is as a 6-ester, and salicylic acid.

The salts may for example be presented as aqueous solutions or as lyophilised powders. The solutions may also be constituted in 0.9% sterile saline. Such solutions may be prepared by the slow addition, with good stirring and under nitrogen, of the requisite amount of the fatty acid or derivative to an aqueous or saline solution of the sugar amine until a clear solution is obtained (pH range: 5 to 9).

The solubilities of some of the lyophilised salts compared to starting EFAs in various solvents are given in Table 2 below, by way of illustration of their physicochemical characteristics:—

TABLE 2

| | Solubilities (w/v) at 25° C. with sonication | |
|---|---|---|
| Solvent | Meglumine Salts of EFAs | EFAs |
| Water | >20% but <40% | <1% |
| Ethanol | >20% but <50% | Miscible in all proportions |
| Chloroform | >20% but <50% | Miscible in all proportions |

In use the salts may be prepared for delivery by oral, parenteral, enteral or other routes. Doses of any one or more of the fatty acids may be 1 mg to 200 g, preferably 10 mg to 20 g and very preferably 50 mg to 2 g/day. When applied topically the concentration of the fatty acid may range from 0.0001 to 50% preferably 0.01 to 30% and very preferably 0.1 to 10% by weight of the preparation.

EXAMPLES OF PREPARATION OF SALTS

EXAMPLE 1

(Meglumine salt of DHA)

N-Methyl glucamine B.P (595.5 mg, 3.05 mmol) is dissolved in pure water (8.0 ml) and, under nitrogen with efficient stirring, there is added, dropwise over 5 mins, z,z,z,z,z,z-docosa-4,7,10,13,16,19-hexaenoic acid, DHA (1.0 g). The mixture is stirred until a clear 20% w/v solution of N-methyl glucammonium/z,z,z,z,z,z-docosa-4,7,10,13,16,19-hexaenoate (Meglumine DHA) is formed. The solution is filtered through a 0.2 μm filter and lyophilisation gives a white waxy powder readily reconstituted in water to a solution of up to 30% w/v.

EXAMPLE 2

(Meglumine salt of GLA)

By proceeding in a similar manner to Example 1 but replacing the DHA with an equivalent amount of z,z,z-octadeca-6,9,12-trienoic acid, GLA, there is formed N-methyl glucammonium z,z,z-octadeca-6,9,12- trienoate (Meglumine GLA) in a 20% w/v aqueous solution.

EXAMPLE 3

(Meglumine salt of DGLA)

By proceeding in a similar manner to Example 1 but replacing the DHA with an equivalent amount of z,z,z-eicosa-8,11,14-trienoic acid, DGLA, there is formed N-methyl glucammonium z,z,z-eicosa-8,11,14-trienoate.

EXAMPLE 4

(Meglumine salt of AA)

By proceeding in a similar manner to Example 1 but replacing the DHA with an equivalent amount of z,z,z,z-eicosa-5,8,11,14-tetraenoic acid, AA, there is formed N-methyl glucammonium z,z,z,z-eicosa-5,8,11,14-tetraenoate (Meglumine AA) in a 20% w/v aqueous solution.

EXAMPLE 5

(Meglumine salt of Ascorbyl GLA)

Hydrogen chloride gas (2.0 g) is bubbled into N,N-dimethyl acetamide (26.5 ml) at 0° C. To the resultant slurry is added a slurry of ascorbic acid (9.69 g) in dichloromethane (13.25 ml) and the mixture is stirred at 0° C. until solution occurs. To this solution at 0° C. under nitrogen, is added z,z,z-octadeca-6,9,12-trienoyl chloride (14.8 g) over a period of 4 hours and the resulting mixture is allowed to stand at the above temperature for 18 hours and room temperature for 1 hour. On cooling to 0° C., ethyl acetate (200 ml) and water (100 ml) are added and the mixture stirred for 1 hour. The organic layer is washed with brine (5×100 ml), dried (Na₂SO₄) and evaporated at 50° C./10 mm Hg then 50° C./0.1 mm/4 hours to give ascorbic acid 6-[(z,z,z)-octadeca-6,9,12-trienoate] (18.25 g, 88%) (ascorbyl GLA) as a pale yellow wax.

A soap-like emulsion of the ascorbyl GLA (112 parts) in pure water (600 parts) is formed by vigorous stirring for 10–15 mins under nitrogen. To this mixture is added with stirring N-methyl glucamine B.P. (66 parts) in pure water (200 parts) over a period of 10–15 mins until a clear solution is obtained. The mixture is filtered through a 0.2 μm filter and then lyophilised to give N-methyl glucammonium 6-(z, z,z-octadeca-6,9,12- trienoyl) ascorbate as a hygroscopic very pale yellow solid.

EXAMPLE 6

(Meglumine salt of Salicylic Acid gamma linolenate)

By proceeding in a similar manner but replacing the ascorbyl GLA with an equivalent amount of 2-(z,z,z-octadeca-6,9,12-trienoyloxy) benzoic acid, which is the GLA derivative of salicylic acid, there is formed N-methyl glucammonium 2-(z,z,z-octadeca-6,9,12-trienoyloxy) benzoate. The GLA derivative of salicylic acid was itself prepared by the following method.

Stage 1: 2,2,2-Trichloroethyl salicylate:— A mixture of salicylic acid (90 g), 2,2,2-trichloroethanol (270 g) and concentrated sulphuric acid (50 g) was stirred and heated at 100° C. for 4 hours. The mixture was diluted with chloroform (800 ml) and extracted with water (2×500 ml). After further extraction with saturated aqueous sodium bicarbonate solution (1000 ml), the organic layer was washed with water (2×500 ml) and dried (Mg SO₄). The chloroform and excess trichloroethanol were removed in vacuo (65° C./20 mm Hg) and the product was distilled (110°–112° C./0.5 mm Hg) to give 2,2,2-trichloroethyl salicylate (104 g, 59%) as a clear liquid which solidified on cooling.

Stage 2: 2,2,2-Trichloroethyl 2-[(z,z,z) octadeca-6,9,12-trienoyloxy] benzoate:— To a solution of 2,2,2-trichloroethyl salicylate (104 g) in dry pyridine (500 ml) at 0–5° C. and under nitrogen was added (z,z,z) octadeca-6,9,12-trienoyl chloride (137.5 g) dropwise over a period of one hour. The reaction mixture was allowed to stir for twenty hours at room temperature and then the pyridine was removed in vacuo (25° C./0.5 mm Hg). The residue was dissolved in diethyl ether (2000 ml) and water (1000 ml) and the resulting two phase system was shaken and acidified slowly to pH1 by addition of 2M hydrochloric acid. The diethyl ether layer was separated and washed with water (4×1000 ml), adding sodium chloride to break any emulsion that formed. After drying the organic layer ($Na_2SO_4$), the solvent was removed in vacuo to give an orange/brown oil. This was subjected to MPLC (Column size: 15 cm dia.×40 cm, Column packing: Matrex silica, pore size 60A, particle size 35–70 μm, Solvent: initially hexane, then 15% diethyl ether in hexane, Fraction size: 1000 ml). The requisite fractions were evaporated in vacuo to give 2,2,2-trichloroethyl-2-[(z,z,z) octadeca-6,9,12-trienoyloxy] benzoate. (189 g, 93% yield) as a pale yellow oil.

Stage 3: 2-[(z,z,z) Octadeca-6,9,12-trienoyloxy] benzoic acid:— 2,2,2-Trichloroethyl-2-[(z,z,z) octadeca-6,9,12-trienoyloxy] benzoate (151 g) was dissolved in a mixture of tetrahydrofuran (750 ml), acetic acid (675 ml) and water (75 ml). Zinc dust (150 g) was added. The mixture was stirred at room temperature under nitrogen for 1.5 hours and then allowed to stand for twenty hours. Excess zinc and zinc salts were filtered off through Celite washing the filter pad with tetrahydrofuran (100 ml) and the filtrate was evaporated at 25° C./10 mm Hg to remove the tetrahydrofuran. The acetic acid and water was then removed at 25° C./0.5 mm Hg. Higher temperatures tend to decompose the product. The resulting oil was dissolved in diethyl ether (1000 ml) and the resulting solution was washed with water (4×200 ml). After drying ($Na_2SO_4$), the ether was evaporated (25° C./10 mm Hg) to give a pale yellow oil which was subjected to a dry column (Packing: Matrex silica (1 Kg), pore size 60A, particle size 35–70 μm, Fraction size: 1000 ml). The requisite fractions were collected, the solvent evaporated as before, the last traces being removed at 25° C./0.1 mm Hg to give 2-[(z,z,z) octadeca-6,9,12,-trienoyloxy] benzoic acid, (77.8 g, 68%) as a pale orange oil which solidified to a wax in the refrigerator.

USE EXAMPLES

1. A sterile solution for topical or local administration containing 0.1–20% by weight of any one of the EFA derivatives of preparative Examples 1 to 4.

2. An oral pharmaceutical preparation containing 100 mg to 1 g in 5 ml of any one of the EFA derivatives of preparative Examples 1 to 6.

3. A sterile pharmaceutical solution for intravenous administration containing 0.1 to 20% by weight of any one of the EFA derivatives of preparative Examples 1 to 6.

4. A skin or hair care preparation containing a concentration of 0.1 to 40% by weight of any one of the EFA derivatives of preparative Examples 1 to 4.

5. A milk, fruit juice or other food or drink preparation containing a concentration of 0.1 to 40% by weight of any one of the EFA derivatives of preparative Examples 1 to 4 or 5.

What is claimed is:

1. A pharmaceutical composition comprising an N-alkylpolyhydroxyamine salt selected from one of the ten n-6 or n-3 essential fatty acids that are beyond the 6-desaturation step, the salt formed with the fatty acid either as such or in the form of a covalent derivative, through the carboxyl group, of a bifunctional compound itself having a free acid function.

2. The pharmaceutical composition according to claim 1 wherein the fatty acid is selected from gamma-linolenic acid, dihomo-gamma-linolenic acid, arachidonic acid, adrenic acid, the 22:5 n-6 acid, stearidonic acid, the 20:4 n-3 acid, eicosapentaenoic acid, the 22:5 n-3 acid and docosahexaenoic acid.

3. A pharmaceutical composition comprising an N-alkylpolyhydroxyamine salt of a polyunsaturated fatty acid, other than those belonging to the n-6 and n-3 series, having 16 to 26 carbon atoms and one to six double bonds, the double bonds being in the cis or trans configuration, the salt being formed with the fatty acid either as such or in the form of a covalent derivative, through the carboxyl group, of a bifunctional compound itself having a free acid function.

4. The pharmaceutical composition according to claim 3 wherein the fatty acid is selected from columbinic acid and alpha-parinaric acid.

5. The pharmaceutical composition according to claim 1 or claim 3 wherein the N-alkhlpolyhydroyamine is N-methylglucamine.

6. The pharmaceutical composition according to claim 1 or claim 3, wherein said bifunctional compound having a free acid function is ascorbic acid or salicylic acid.

7. A nutritional supplement comprising an N-alkylpolyhydroxyamine salt of an n-6 or n-3 essential fatty acid that is beyond the 6-desaturation step, the salt being formed with the fatty acid either as such or in the form of a covalent derivative, through the carboxyl group, of a bifunctional compound itself having a free acid function.

8. A nutritional supplement according to claim 7 wherein the fatty acids are selected from gamma-linolenic acid, dihomo-gamma-linolenic acid, arachidonic acid, adrenic acid, the 22:5 n-6 acid, stearidonic acid, the 20:4 n-3 acid, eicosapentaenoic acid, the 22:5 n-3 acid and docosahexaenoic acid.

9. A nutritional supplement comprising an N-alkylpolyhydroxyamine salt of a polyunsaturated fatty acid, other than those belonging to the n-6 and n-3 series, having 16 to 26 carbon atoms and one to six double bonds, the double bonds being in the cis or trans configuration, the salt being formed with the fatty acid either as such or in the form of a covalent derivative, through the carboxyl group, of a bifunctional compound itself having a free acid function.

10. The nutritional supplement according to claim 9 wherein the fatty acid is selected from columbinic acid and alpha-parinaric acid.

11. The nutritional supplement according to claim 7 or claim 9 wherein the N-alkylpolyhydroxyamine is N-methylglucamine.

12. The nutritional supplement according to claim 7 or claim 9, wherein said bifunctional compound having a free acid function is ascorbic acid or salicylic acid.

* * * * *